United States Patent [19]

Lemley et al.

[11] Patent Number: 5,453,271
[45] Date of Patent: Sep. 26, 1995

[54] VACCINE AGAINST RICIN TOXIN

[75] Inventors: Paul V. Lemley, Gettysburg, Pa.;
Donald A. Creasia, Frederick, Md.

[73] Assignee: The United States of America as represented by the Secretary of the Army, Washington, D.C.

[21] Appl. No.: 82,422

[22] Filed: Jun. 28, 1993

[51] Int. Cl.$^6$ .......................... A61K 39/00; A61K 39/38; A61K 39/395; A61K 39/40; A61K 39/42; A61K 49/44

[52] U.S. Cl. ................................. 424/184.1; 424/183.1; 424/178.1

[58] Field of Search ............................ 424/88, 92, 184.1, 424/183.1, 178.1

[56] References Cited

U.S. PATENT DOCUMENTS

| | | | |
|---|---|---|---|
| 4,459,287 | 7/1984 | Shionoya et al. | 424/88 |
| 4,490,362 | 12/1984 | Shionoya et al. | 424/177 |
| 4,689,401 | 8/1987 | Ferris | 530/396 |
| 4,962,188 | 10/1990 | Frankel | 530/389 |

OTHER PUBLICATIONS

Lemley et al. 1992. Mice are actively immunized after passive monoclonal antibody . . . Immunology 76(3):511–3.
Pincus et al., 1990, Variants selected by treatment of human immunodeficiency virus-infected cells with an immunotoxin, J. Exp. Med., 172:745–757.
Pimm et al, 1989, The influence of syngeneic anti-idiotypic antibody on the biodistribution of an anti-tumour monoclonal antibody in BALB/c mice, Int. J. Cancer, 43(1):147–151.

Primary Examiner—Christine M. Nucker
Assistant Examiner—Nita M. Minnifield
Attorney, Agent, or Firm—John F. Moran; Anthony T. Lane

[57] ABSTRACT

It is now possible to immunize susceptible mammals against the pathological effect of exposure to rice, including inhalation of ricin, by administration of an immunogenic effective amount of ricin toxin sub-units, including subunits of both the A chain and the B chain of the ricin toxin given separately to provide safe, efficacious protection.

7 Claims, No Drawings

VACCINE AGAINST RICIN TOXIN

FIELD OF THE INVENTION

This application relates to a vaccine to elicit antibody protection against pathological effects of exposure to ricin toxin.

BACKGROUND OF THE INVENTION

Ricin is a very toxic protein obtained from the castor bean seeds. Ricin is a glycoprotein with a molecular weight of about 64–65 kD composed of an A chain having a weight of about 31 kD and a B chain having a molecular weight of about 33 kD. The A chain functions to inactivate ribosome and inhibit protein synthesis of cells.

Each of the toxin's two subunits has a distinct role in toxicity. The B chain selectively binds to residual groups of galactose on the membrane surfaces of eukaryotic cells. The toxin is able to access the cytosol. It has been postulated that the toxin can enter the cytosol from an intracellular compartment not accessible to extracellular antibodies (Sandvig, et al ((*J. Biol. Chem.* 257, 7504–7513 (1982)).

The study of the ricin B subunit in translocation of the ricin into the cytosol has been studied fairly extensively. It has been proposed that intracellular galactose receptors mediate the effect of the ricin B. Antibodies to the ricin B chain have been shown to protect against the pathological effects of ricin toxin. U.S. Pat. No. 4,520,011 to Neville, et al. discloses and claims a method of inhibiting protein synthesis in target cells by addition of excess ricin B to compositions containing ricin A chain attached to antibodies that target particular cells. By adding an excess of ricin B chain it was possible to increase the effect of the targeting antibody/ricin A complex on the target cells. This increase in effect on target cells was attributed to the effect of ricin B in facilitating entry of ricin A into the cytosol of the targeted cell.

U.S. Pat. No. 4,490,362 to Shionoya, et al. teaches use of the B chain of ricin as a generalized immunopotentiator to increase immune response to infectious diseases. That reference does not suggest use of the B chain alone as a vaccine against ricin toxin.

Compositions containing either the A chain of ricin or the B chain of ricin are available commercially. Recombinant A chain has been made by recombinant methods. (See, for example, U.S. Pat. No. 4,689,401 to Ferris, which is incorporated herein by reference in its entirety.) The use of the A chain in medicinal science wherein the A chain is coupled with a targeting moiety to target to particular cells as a means of selectively destroying malignant cells is known. The ricin A chain has, in some instances, been modified when used in a conjugate for purposes of selective destruction. See, for example, U.S. Pat. No. 4,980,457 to Jansen and Gros and U.S. Pat. No. 4,962,188 to Frankel. However, the use of the ricin A chain in a vaccine to provide immunogenic activity to elicit antibody response for protection against the pathological effects of exposure to the complete ricin has not been known.

A first generation ricin toxoid vaccine composed of ricin toxin that has been treated with formaldehyde has been developed and is in pre-clinical evaluation. While the efficacy of this vaccine appears to be adequate, safety concerns center on three issues: 1) Highly lethal toxin is used as a starting material; 2) potential for reversion exists; and (3) involvement of formaldehyde in conjunction with heat in the treatment and stabilization of the vaccine preparation can lead to unacceptable side effects and a rather variable product.

The exact sequence of the ricin toxin A chain (RTA) can vary in nature from one variety of castor bean seed to another.

SUMMARY OF THE INVENTION

This invention provides a vaccine preparation to be given to immunize susceptible mammals against the pathological effects of exposure to ricin, including inhalation of ricin, by administration of an immunogenic effective amount of ricin toxin sub-units, including subunits of both the A chain and the B chain of the ricin toxin. In a preferred embodiment the active agent used is the A chain (RTA) which may be administered in a pharmaceutically acceptable carrier with or without an adjuvant. Dosages of 1 µg to 1000 µg are appropriate. A preferred dosage range is 1 µg to 100 µg of the RTA. The antigenic RTA is most effective if repeated doses are administered. In a preferred embodiment, the appropriate dosage is administered three times at two week intervals.

DETAILED DESCRIPTION OF THE INVENTION

The use of sub-units (A chain and B chain of the ricin toxin) was attempted to address concerns about the safety and efficacy of the prior art vaccines to protect from pathological effects of exposure to Ricin toxin. Since the sub-units are far less toxic than ricin (2–6 logs difference in toxicity) it was thought that use of subunits would provide reliable protection against the ricin toxin without exposure to untoward side effects.

The problems encountered in use of sub-units varied. It was found that the ricin A chain was very sensitive to treatment with formalin. When the ricin A chain is treated with formalin, it is possible to inactivate toxic properties by use of formalin alone without heating.

It is possible to protect susceptible mammals with either the A or B chain. Vaccination by ricin B chain will protect from systemic challenge, but will not protect from aerosol challenge with the ricin whole toxin. When the animals vaccinated with only the B chain survive (infrequently) aerosol challenge there is always measurable titer to ricin A chain in their sera. When ricin A chain (RTA) is used to immunize, protection against both systemic and aerosol challenge is effected. Hence, the immunization using ricin A chain is a preferred form of protection against pathological effects of ricin toxin. During preliminary studies, administrations of ricin B chain and ricin A chain were studied.

EXAMPLE 1

Untreated ricin chains A and B were introduced separately into mice, with the A chain being administered at a dosage of 5.0 µg/mouse/injection and the B chain administered at dosage of 3.0 µg/mouse/injection. The time between administration of the separate subunits varied from 24 hour to 7 days. The protective response was assessed by exposing the mice to challenge with lethal ricin aerosol. The results are shown below:

| Time between dosing with A chain and B chain | Survival rate |
| --- | --- |
| 24 hrs. | 6/7 |
| 48 hrs. | 5/5 |
| 7 days | 4/4 |
| Controls: | 0/8 |

A second test employed the administration of B chain followed in two days by administration of A chain. The administration of the dosages with the two day separation between the chains was repeated with one week between the first administration of the A chain and the second administration of the B chain followed by a third similar dosing. Twelve days after the administration of the last dose of A chain the mice were challenged with aerosol ricin. All twelve animals survived.

The two component chains of the ricin toxin may be purchased separately ($\geq$99% pure). Systemically each of the chains can be shown to be at least two logs less toxic than the native toxin. When both untreated chains were introduced simultaneously death resulted. Co-introduction of one treated and one untreated chain or two treated chains leads to active immunity. When the untreated A and B chains are introduced separately with at least a 24 hour interval between introduction of the second chain, active immunity resulted without lethal results. The order of introduction of the chains is not important. When there was co-introduction of one treated and one untreated chain or of two chains wherein both chains had been treated with formalin the animals developed effective immunity without lethal effects. It is suggested that timed release using biodegradable polymer could be administered together if the system avoids administration of both A chain and B chain in such close proximity that both would be present in the host at the same time.

EXAMPLE 2

Ricin A chain only was used to immunize mice with dosages of 5.0 μg/mouse/injection and 3.0 μg/mouse/injection being administered. Repeat dosages were administered two weeks apart.

| Dosage | Number of doses | Results |
| --- | --- | --- |
| 5.0 μg | 2 | 1/5 |
| Control | | 0/8 |
| 3.0 μg | 3 | 5/12 |
| Control | | 0/10 |

When the immunizations were administered three times at two week intervals at dosage of 5.0 μg/mouse/injection, all mice in four independent tests survived challenge with aerosol administration of ricin. Hence, it is seen that with administration of only ricin A chain (RTA) it is possible to provide effective immunization against the lethal effects of aerosol administered ricin without use of the B chain as an antigen. It is also seen that the survival is related to dosage amount and number of doses administered.

The antigenic agents of the invention may be administered by any means that will result in the active agent contacting tissue capable of immune response. Administration may be, for example, by injection (for example, subcutaneous, intradermal, or intramuscular), by contact with the nasopharyngeal mucosa, or by application to abraded dermal tissue. The compositions for administration may contain adjuvants such as alum.

The administration of RTA alone or preceded by or followed by administration of the B chain or administration of the treated, separate chains to larger animals or to cells in vitro can also be used to elicit antibodies for administration to non-protected patients who have been exposed to the ricin toxin. Because the chains administered separately are far less toxic, the living systems used to provide the antibodies are not adversely affected thereby.

The sub-units used for protection by methods of the invention can also be produced in culture by recombinant means known in the art. Eukaryotic cells, *E. coli* and yeast are suggested cells use in making recombinant RTA. A example of such production is seen in U.S. Pat. No. 4,689,401 to Ferris, which is incorporated herein by reference. Equivalents of the native RTA should contain the fragment which interacts with the 60S ribosome.

We claim:

1. A method of immunizing a mammal against the pathogenic effects of ricin toxin by administration of a composition of matter comprising an antigenic effective amount of ricin A chain and essentially free of ricin B chain in a pharmaceutically acceptable carrier.

2. A method of claim 1, wherein the dosage administered is between 1 μg and 1000 μg of ricin A chain.

3. A method of claim 2, wherein the dosage administered is between 1 μg and 100 μg of ricin A chain.

4. A method of claim 1, wherein the immunizing effective amount of ricin A chain administered at least twice.

5. A method of claim 1 wherein three doses of ricin A chain are administered.

6. A method of claim 4, wherein the dosage administered is between 1 μg and 1000 μg.

7. A method of claim 6, wherein the dosage administered is between 1 μg and 100 μg.

\* \* \* \* \*